US009060686B2

(12) United States Patent
Abe

(10) Patent No.: US 9,060,686 B2
(45) Date of Patent: Jun. 23, 2015

(54) ULTRASOUND DIAGNOSTIC APPARATUS AND ULTRASOUND IMAGE PROCESSING METHOD

(75) Inventor: Yasuhiko Abe, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1321 days.

(21) Appl. No.: 11/180,608

(22) Filed: Jul. 14, 2005

(65) Prior Publication Data

US 2006/0036172 A1 Feb. 16, 2006

(30) Foreign Application Priority Data

Jul. 16, 2004 (JP) ................................ 2004-210110

(51) Int. Cl.

| | |
|---|---|
| ***A61B 5/00*** | (2006.01) |
| ***A61B 8/14*** | (2006.01) |
| ***A61B 8/08*** | (2006.01) |
| ***A61B 8/13*** | (2006.01) |
| ***A61B 8/00*** | (2006.01) |
| ***G01S 7/52*** | (2006.01) |
| ***G01S 15/89*** | (2006.01) |

(52) U.S. Cl.

CPC ................ *A61B 5/0048* (2013.01); *A61B 8/14* (2013.01); *A61B 8/08* (2013.01); *A61B 8/0883* (2013.01); *A61B 8/13* (2013.01); *A61B 8/461* (2013.01); *A61B 8/485* (2013.01); *G01S 7/52087* (2013.01); *G01S 15/8979* (2013.01)

(58) Field of Classification Search

CPC ........ A61B 8/0083; A61B 8/485; A61B 8/14; A61B 5/0048

USPC ................................ 600/443, 437, 440, 438

See application file for complete search history.

(56) References Cited

U.S. PATENT DOCUMENTS

| | | | | |
|---|---|---|---|---|
| 5,456,255 A * | 10/1995 | Abe et al. | ...................... | 600/443 |
| 5,622,174 A * | 4/1997 | Yamazaki | ...................... | 600/441 |
| 5,671,744 A * | 9/1997 | Abe et al. | ...................... | 600/443 |
| 5,785,654 A * | 7/1998 | Iinuma et al. | ................ | 600/441 |
| 5,913,824 A * | 6/1999 | Ogasawara et al. | ........... | 600/455 |
| 6,053,869 A * | 4/2000 | Kawagishi et al. | ........... | 600/443 |

(Continued)

FOREIGN PATENT DOCUMENTS

| | | |
|---|---|---|
| JP | 6-114059 | 4/1994 |
| JP | 6-285066 | 10/1994 |

(Continued)

OTHER PUBLICATIONS

U.S. Appl. No. 11/534,116, filed Sep. 21, 2006, Abe, et al.

Japanese Office Action mailed Feb. 5, 2013 for Patent Application No. 2011-049612 (with English translation).

*Primary Examiner* — Rochelle Turchen

(74) *Attorney, Agent, or Firm* — Oblon, McClelland, Maier & Neustadt, L.L.P.

(57) ABSTRACT

An ultrasound diagnostic apparatus which performs diagnosis of a subject to be examined by using an ultrasound probe which emits ultrasound waves and receives the ultrasound waves reflected by the subject, includes a measuring section which measures a motion velocity of local tissue of the subject by using an ultrasound waves transmitted/received by the ultrasound probe, an acquiring section which acquires motion information representing a strain or displacement of the tissue on the basis of the motion velocity, and a calculating section which calculates a parameter value representing a change amount of motion of the tissue with a change in load on the basis of two pieces of motion information acquired by the acquiring section in two load states in which different loads are applied to the subject.

20 Claims, 13 Drawing Sheets

(56) References Cited

U.S. PATENT DOCUMENTS

| | | | | |
|---|---|---|---|---|
| 6,638,221 | B2 | 10/2003 | Abe et al. | |
| 6,957,095 | B2 * | 10/2005 | Matsui | 600/407 |
| 2003/0013963 | A1 * | 1/2003 | Bjaerum et al. | 600/443 |
| 2003/0083578 | A1 * | 5/2003 | Abe et al. | 600/447 |
| 2005/0085729 | A1 | 4/2005 | Abe | |
| 2007/0167777 | A1 * | 7/2007 | Abe et al. | 600/441 |

FOREIGN PATENT DOCUMENTS

| | | |
|---|---|---|
| JP | 10-262970 | 10/1998 |
| JP | 11-000327 | 1/1999 |
| JP | 11-155862 | 6/1999 |
| JP | 3187008 | 5/2001 |
| JP | 2003-79627 | 3/2003 |
| JP | 2003-175041 | 6/2003 |

* cited by examiner

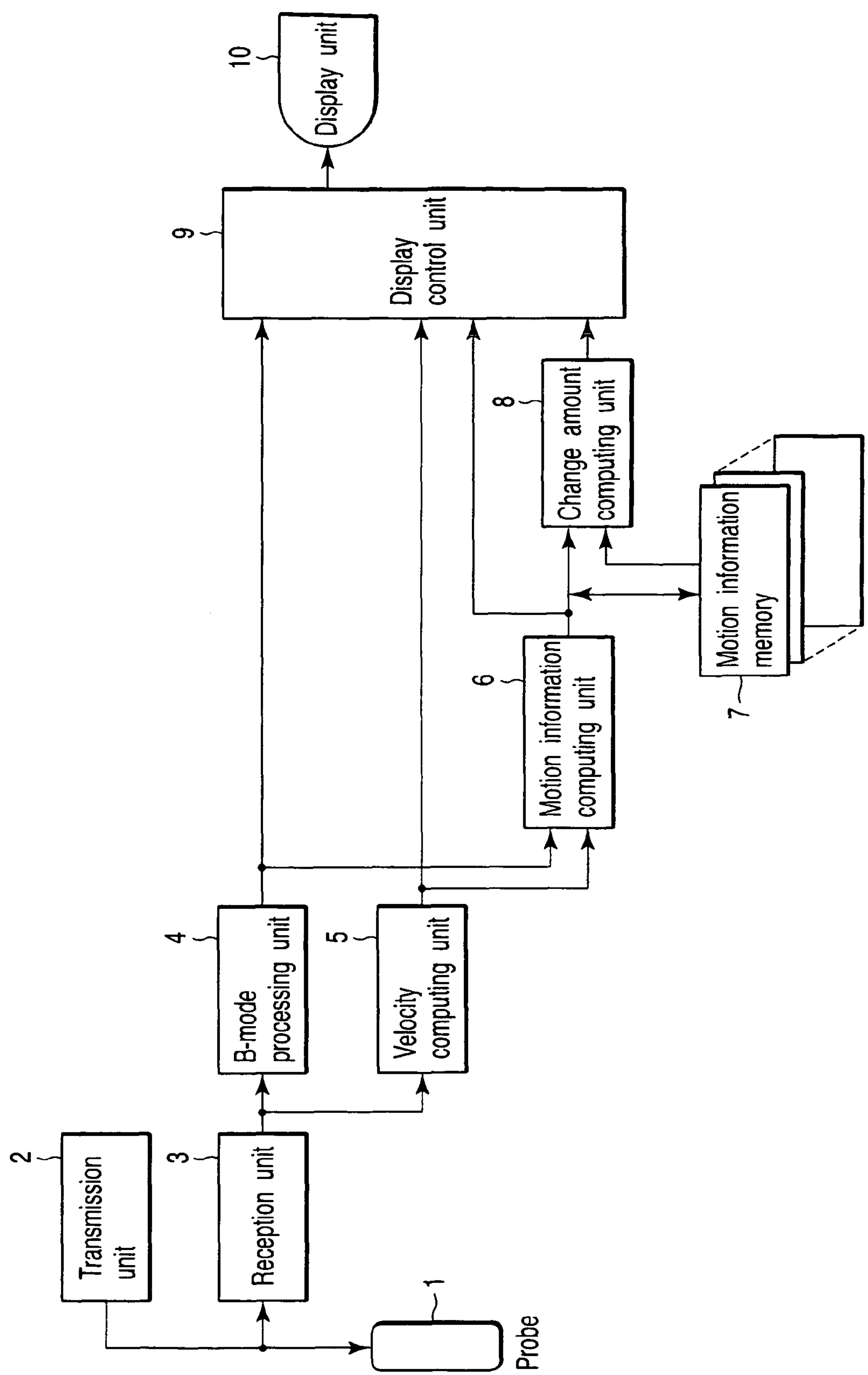
F I G. 1

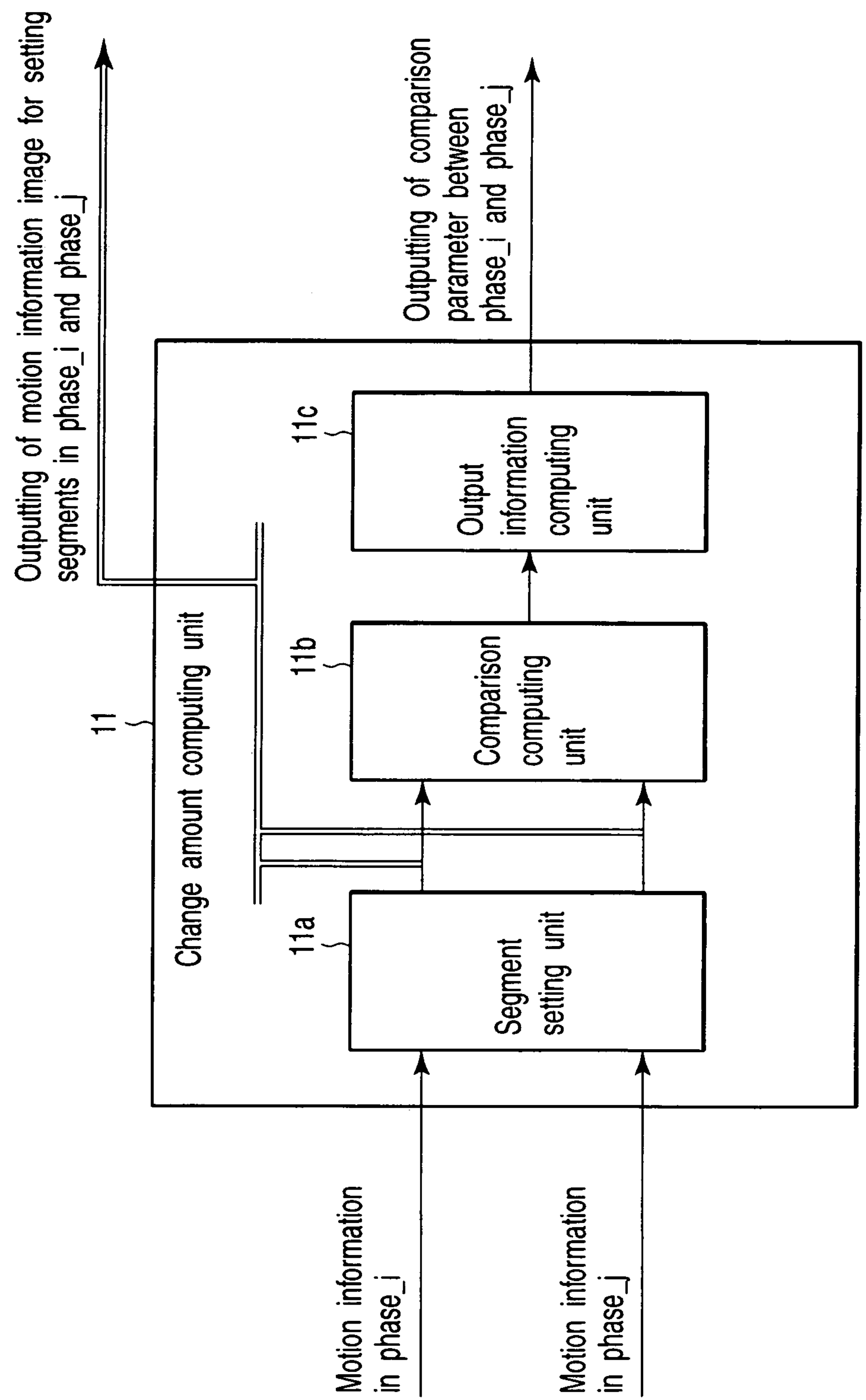
F I G. 5

Example of ROIs
(pseudo-ASE-segment)

Example of ASE-segment
(short-axis image)

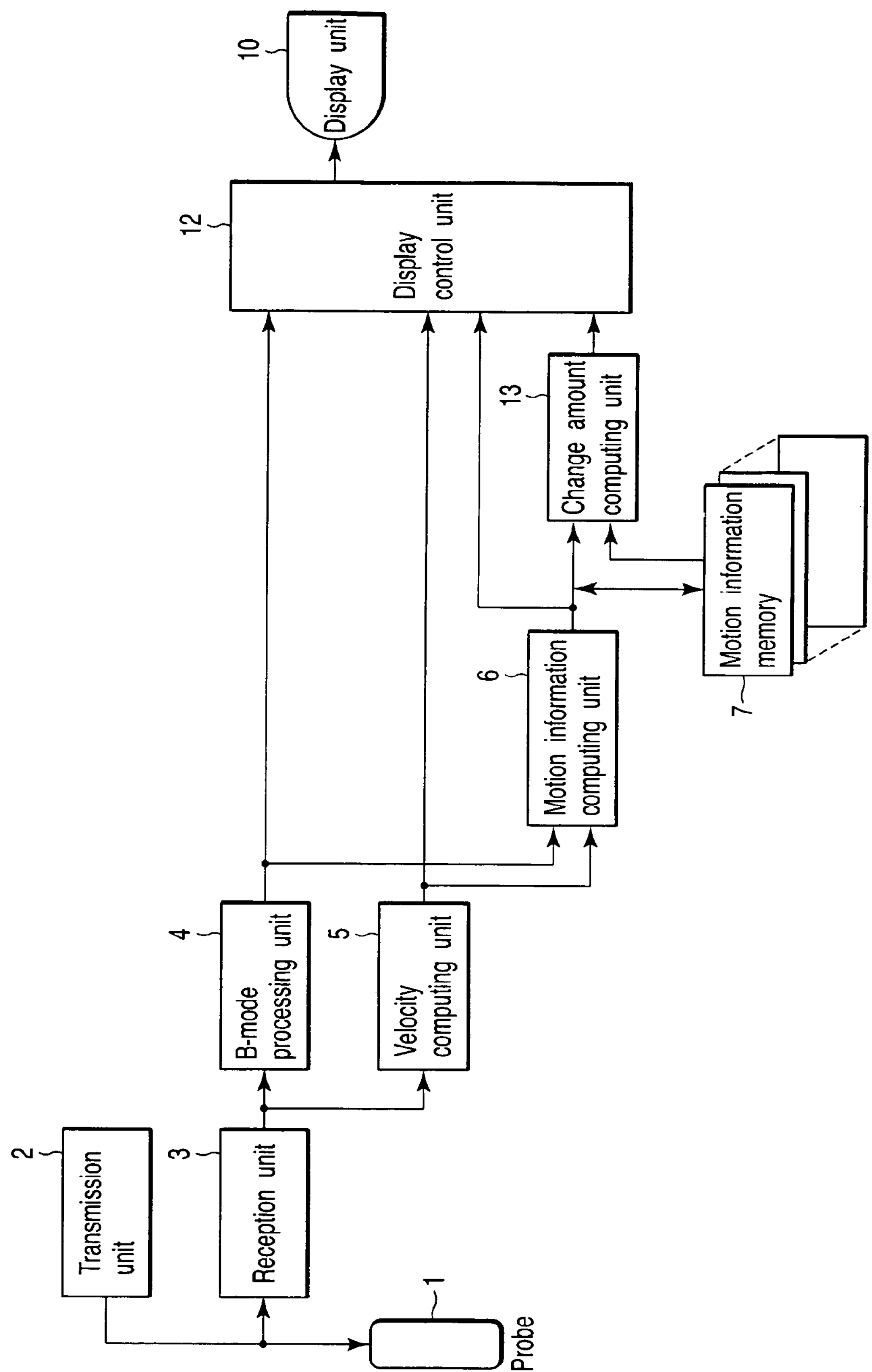
F I G. 8

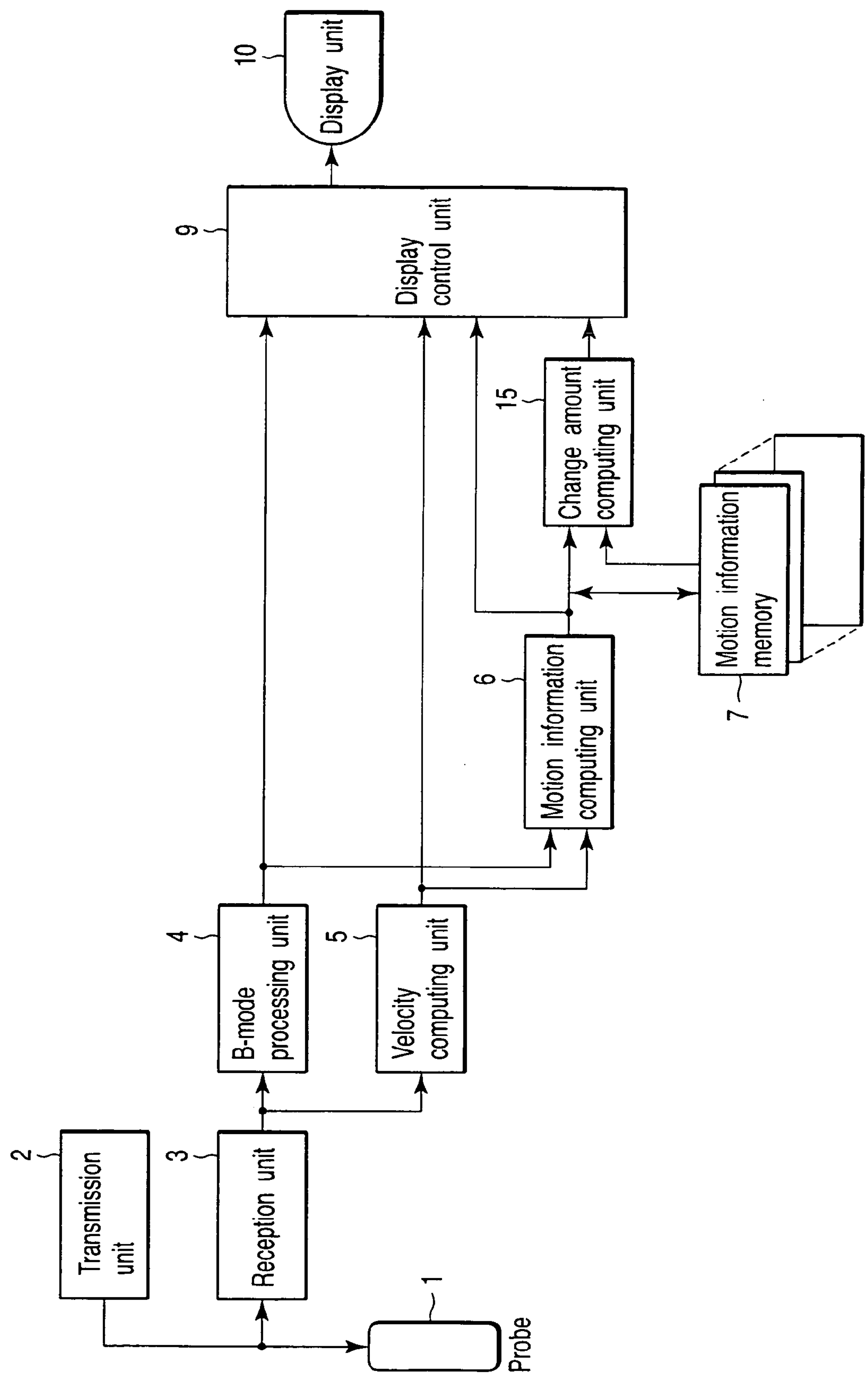
F I G. 1 0

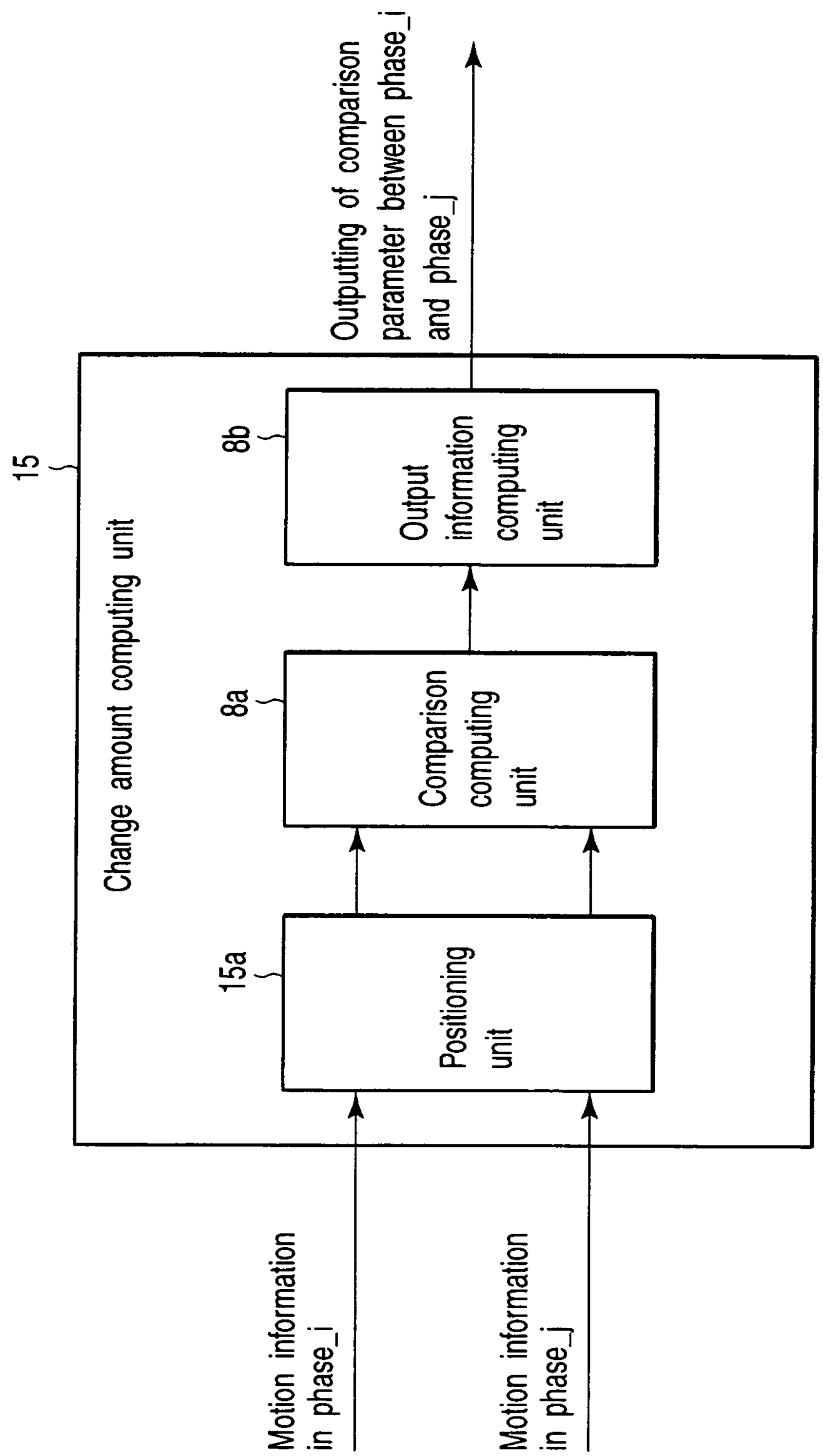
F I G. 11

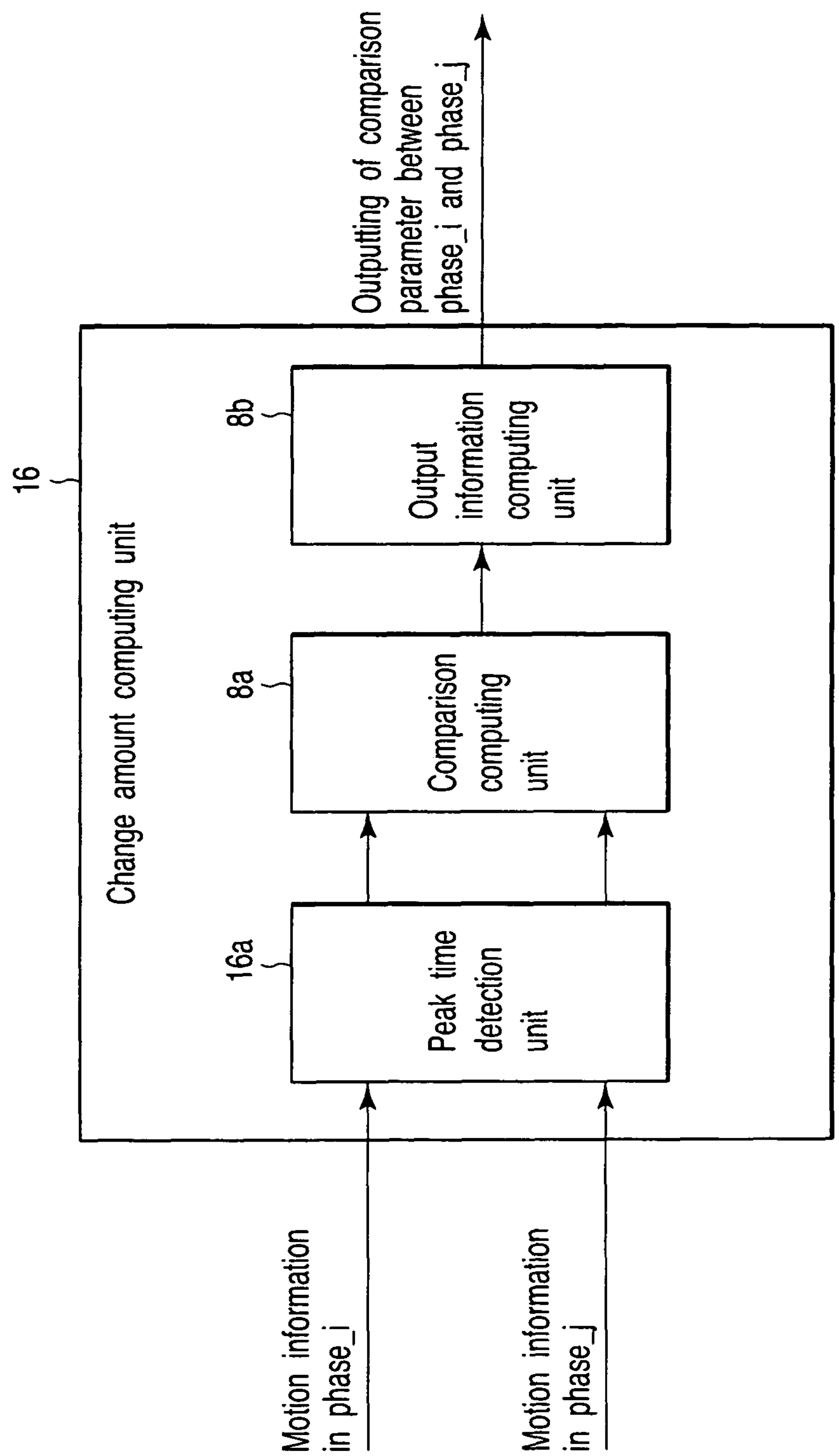
F I G. 1 3

ULTRASOUND DIAGNOSTIC APPARATUS AND ULTRASOUND IMAGE PROCESSING METHOD

CROSS-REFERENCE TO RELATED APPLICATIONS

This application is based upon and claims the benefit of priority from prior Japanese Patent Application No. 2004-210110, filed Jul. 16, 2004, the entire contents of which are incorporated herein by reference.

BACKGROUND OF THE INVENTION

1. Field of the Invention

The present invention relates to an ultrasound diagnostic apparatus and ultrasound image processing method which estimate the speed of living tissue such as cardiac muscle by using ultrasound waves, and output the local motion information of the tissue by processing the estimated velocity information, thereby providing information effective for medical diagnosis.

2. Description of the Related Art

With regard to living tissue such as cardiac muscle, it is very important for the diagnosis of the tissue to objectively and quantitatively evaluate its function.

Various kinds of quantitative evaluation methods have been tried. A stress echo method using an ultrasound diagnostic apparatus has recently attracted attention. In this method, for example, a subject to be examined is made to jog, and images of the cardiac muscle are taken before and after jogging. These images are then compared with each other to make diagnosis on a region having abnormality.

In this type of examination, it is preferable to avoid diagnosis based on the subjectivity of an examiner by quantifying comparison before and after the application of a stress (load). Various methods have been proposed for this purpose.

For example, a method using a dedicated left ventricular wall motion analysis apparatus is known. An ultrasound diagnostic apparatus which can easily and accurately perform diagnosis by the stress echo method is also disclosed in Jpn. Pat. Appln. KOKAI Publication No. 6-285066. In addition, a method which can mainly image how local delay of wall motion occurs for each region is disclosed in Japanese Patent No. 3187008.

In the method using the dedicated left ventricular wall motion analysis apparatus, tracing or the like of an endocardium is required, and complicated operation is required.

Velocity information on a living organ tends to become unstable due to the influences of speckle noise and the like. Acceleration information is further susceptible to the influence of noise. According to the ultrasound diagnostic apparatus disclosed in Jpn. Pat. Appln. KOKAI Publication No. 6-285066, since such information is compared, it is difficult to obtain a stable result with high reproducibility.

In an ischemic heart disease case, even if a wall motion looks normal before the application of a load, ischemia is induced by the application of the load, and local delay of the wall motion may occur. The method disclosed in Japanese Patent No. 3187008 performs no comparison before and after the application of a load unlike in the stress echo method. For this reason, it is not easy to detect a slight change in the state of local delay described above before and after the application of a load.

BRIEF SUMMARY OF THE INVENTION

Under the circumstances, it has been required to perform diagnosis by the stress echo method which can be easily executed with high reproducibility by obtaining highly stable, useful diagnosis information.

According to a one aspect of the present invention, there is provided an ultrasound diagnostic apparatus which performs diagnosis of a subject to be examined by using an ultrasound probe which emits ultrasound waves and receives the ultrasound waves reflected by the subject, comprising: a measuring section which measures a motion velocity of local tissue of the subject by using an ultrasound waves transmitted/received by the ultrasound probe; an acquiring section which acquires motion information representing a strain or displacement of the tissue on the basis of the motion velocity; and a calculating section which calculates a parameter value representing a change amount of motion of the tissue with a change in load on the basis of two pieces of motion information acquired by the acquiring section in two load states in which different loads are applied to the subject.

According to a one aspect of the present invention, there is provided an ultrasound image processing method of performing image processing for diagnosis of a subject to be examined on the basis of a motion velocity measured with respect to local tissue in the subject by using ultrasound waves transmitted/received by an ultrasound probe, comprising: acquiring motion information representing a strain or displacement of the tissue on the basis of the motion velocity; and calculating a parameter value representing a change amount of motion of the tissue with a change in load on the basis of two pieces of motion information acquired in two load states in which different loads are applied to the subject.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an ultrasound diagnostic apparatus according to the first embodiment of the present invention;

FIG. 5 is a block diagram showing the concrete arrangement of a change amount computing unit in FIG. 4;

FIG. 8 is a block diagram showing the arrangement of an ultrasound diagnostic apparatus according to the third embodiment of the present invention;

FIG. 10 is a block diagram showing the arrangement of an ultrasound diagnostic apparatus according to the fourth embodiment of the present invention;

FIG. 11 is a block diagram showing the concrete arrangement of a change amount computing unit in FIG. 10;

FIG. 13 is a block diagram showing the concrete arrangement of a change amount computing unit in FIG. 12;

DETAILED DESCRIPTION OF THE INVENTION

Figure 2:
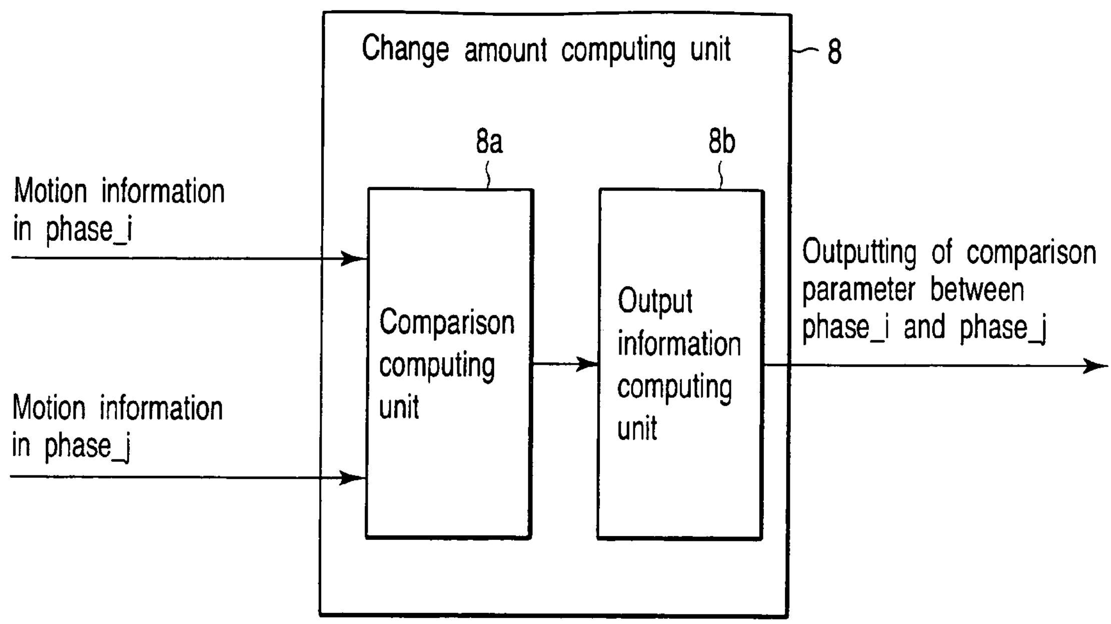
FIG. 2 is a block diagram showing the concrete arrangement of a change amount computing unit in FIG. 1.

The embodiments of the present invention will be described below with reference to the views of the accompanying drawing.

First Embodiment

FIG. 1 is a block diagram showing the arrangement of an ultrasound diagnostic apparatus according to the first embodiment.

As shown in FIG. 1, the ultrasound diagnostic apparatus of the first embodiment includes an ultrasound probe 1, transmission unit 2, reception unit 3, B-mode processing unit 4, velocity computing unit 5, motion information computing unit 6, motion information memory 7, change amount computing unit 8, display control unit 9, and display unit 10.

The ultrasound probe 1 comprises an ultrasound transducer array of a plurality of ultrasound transducers which convert electrical signals into ultrasound waves. The ultrasound probe 1 transmits/receives ultrasound waves by using the ultrasound transducer array. Assume that the ultrasound probe 1 in the first embodiment is a sector probe designed for cardiac examination.

The transmission unit 2 generates a driving signal with a predetermined delay characteristic for each ultrasound transducer so as to form an ultrasound beam toward a scan line. The reception unit 3 generates an ultrasound echo signal corresponding to the scan line by performing delay addition processing for an ultrasound echo signal output from each ultrasound transducer of the ultrasound transducer array.

The B-mode processing unit 4 generates a B-mode signal corresponding to the amplitude intensity of an ultrasound echo by performing envelope detection processing for an ultrasound echo signal output from the reception unit 3. The B-mode processing unit 4 generates a B-mode ultrasound image representing the two-dimensional distribution of the B-mode signal applied to a predetermined slice.

The velocity computing unit 5 obtains a spatiotemporal distribution image of the tissue velocity from the ultrasound echo signal having undergone the delay addition processing. As a technique to be used by the velocity computing unit 5 to obtain a spatiotemporal distribution image, a known technique such as a tissue Doppler processing technique or the technique disclosed in Jpn. Pat. Appln. KOKAI Publication No. 08-164139 can be used. The tissue Doppler processing technique is a technique suitable for the acquisition of a one-dimensional tissue speed in the ultrasound beam direction. Jpn. Pat. Appln. KOKAI Publication No. 08-164139 discloses a technique of acquiring a two-dimensional tissue velocity by movement vector processing having processing such as processing by a pattern matching technique.

The motion information computing unit 6 obtains the motion information of tissue from a B-mode ultrasound image and spatiotemporal distribution image. As a technique to be used by the motion information computing unit 6 to obtain motion information, the technique disclosed in Jpn. Pat. Appln. KOKAI Publication No. 2003-175041 can be used. That is, motion information about a local displacement or strain is obtained on the basis of local time integration processing using a tissue speed. The motion information computing unit 6 outputs as the value of each pixel(x, y) a motion information image with the motion information obtained in the above manner. The motion information image output from the motion information computing unit 6 contains the B-mode information which was referred to for the generation of the image. The motion information memory 7 stores the motion information image obtained by the motion information computing unit 6. The motion information memory 7 stores motion information images in a plurality of examination states (to be referred to as phases hereinafter) wherein the subject is in different load states.

The change amount computing unit 8 calculates the change amount (to be referred to as a comparison parameter hereinafter) of two pieces of motion information in different phases which are stored in the motion information memory 7.

The display control unit 9 generates a display image on the basis of the B-mode ultrasound image, the spatiotemporal distribution image, motion information, and the comparison parameter. The display unit 10 displays the display image generated by the display control unit 9.

FIG. 2 is a block diagram showing the concrete arrangement of the change amount computing unit 8.

As shown in FIG. 2, the change amount computing unit 8 includes a comparison computing unit **8*a* and output information computing unit 8*b***.

The comparison computing unit **8*a* generates the comparison parameter by comparing motion information images by using the pieces of motion information in different phases which are stored in the motion information memory 7. The output information computing unit 8*b* generates a comparison parameter image on the basis of the value of the comparison parameter generated by the comparison computing unit 8*a***.

The operation of the ultrasound diagnostic apparatus having the above arrangement will be described next.

The application of the present invention to the evaluation of the local motion of the cardiac tissue using 2D images will be described below.

[1. Acquisition of Tissue Velocity]

First of all, a spatiotemporal distribution image of the tissue velocity (a two-dimensional distribution image for each time) is obtained by the speed computing unit 5.

[2. Acquisition of Motion Information]

Motion information about the local displacement or strain of the tissue is obtained from the tissue velocity by the motion information computing unit 6.

[3. Acquisition of Pieces of Motion Information in Different Load States]

A plurality of phases are set, and the above acquisition of motion information is performed for each phase. A motion information image in each phase is stored in the motion information memory 7.

In this case, loads are roughly classified into exercise loads and drug (dobutamine) loads. In stress diagnosis based on an exercise load, three phases are generally set, namely "before application of load", "during application of load (peak load time)", and "after application of load (recovery)". With regard to the application of a dobutamine load, six phases are generally set, namely "before application of load", "10 γ load", "20 γ load", "30 γ load", "40 γ load (peak load time)", and "after application of load (recovery)". The simplest stress diagnosis is performed by comparison between "before application of load" and "during application of load (peak load time)". That is, the minimum necessary phases are the two phases "before application of load" and "peak load time".

[4. Acquisition of Comparison Parameter]

The change amount computing unit 8 acquires a comparison parameter from motion information images stored in the motion information memory 7. A change in tissue motion is observed as a change between two different phases regardless of how phases are set for stress diagnosis. The change amount computing unit 8 therefore acquires a comparison parameter on the basis of motion information images in two arbitrary phases, i.e., phase_i and phase_j, stored in the motion information memory 7.

Figure 3:
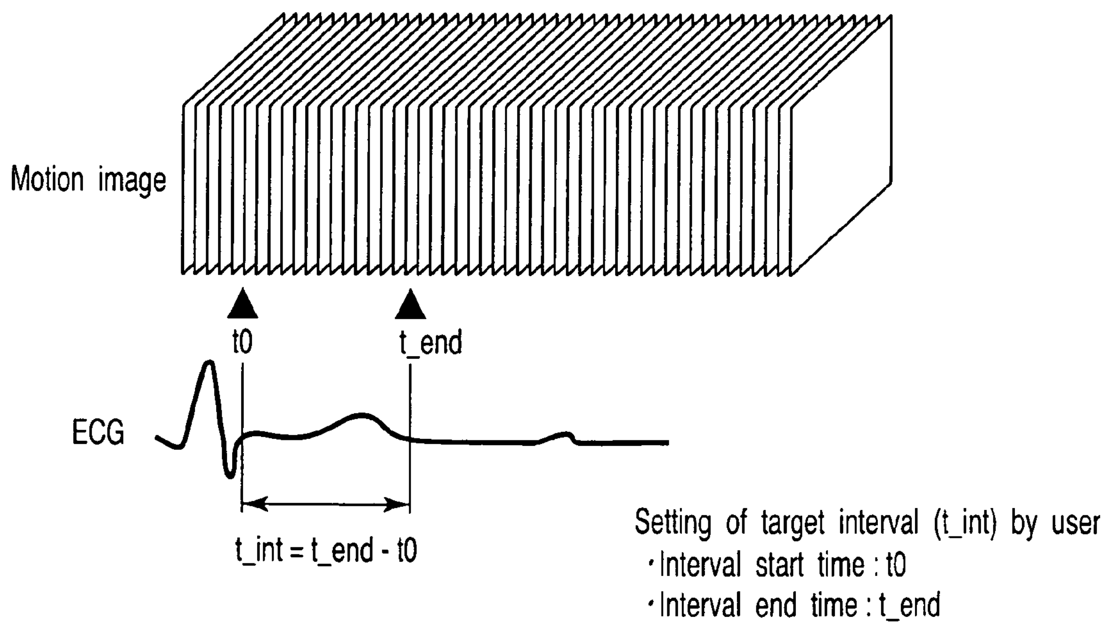
FIG. 3 is a view showing how a cardiac time interval t_int is set, in which the peak value of motion information is to be detected.

The comparison computing unit 8*a* of the change amount computing unit 8 preferably obtains a peak value (maximum or minimum value) of each pixel(x, y) of a motion information image in a predetermined cardiac time interval t_int like that shown in FIG. 3. The comparison computing unit 8*a* obtains Vmax(i, x, y) as a peak value in phase_i, and obtains Vmax(j, x, y) as a peak value in phase_j. Note that the cardiac time interval t_int is determined by, for example, making the user designate an interval start time t0 and interval end time t_end.

The comparison computing unit 8*a* then computes a comparison parameter according to one of expressions (1), (2), and (3) given below:

$$V\max(j,x,y)/V\max(i,x,y) \quad (1)$$

$$V\max(j,x,y)-V\max(i,x,y) \quad (2)$$

$$\{V\max(j,x,y)-V\max(i,x,y)\}/V\max(i,x,y) \quad (3)$$

Note that one of expressions (1), (2), and (3) may be selected in the design stage of an ultrasound diagnostic apparatus, and the comparison computing unit 8*a* may be configured to permanently compute the selected expression. Alternatively, the comparison computing unit 8*a* may be equipped with a function of performing computations based on two or three arbitrary expressions of expressions (1), (2), and (3) so as to selectively execute the computations in accordance with a user instruction.

[5. Display of Comparison Parameter]

The output information computing unit 8*b* generates a comparison parameter image indicating the value of the comparison parameter computed in the above manner.

The display control unit 9 generates a display image superimposed on a B-mode image by color-converting the comparison parameter image generated by the output information computing unit 8*b*, like velocity display by a tissue Doppler image or motion information image display of a displacement or strain. This display image is displayed by the display unit 10. Note that for such a comparison parameter image, a color map different from that used for a velocity, or a displacement or strain is preferably used.

Assume that, for example, the color map to be used is designed to express the sign "+" of the change amount, given by expression (3), by a warm color (e.g., red), the sign "−" by a cold color (e.g., blue), and the magnitude of the change amount by hue (or luminance). Assume that such a color map is used, and a load is applied to a patient who exhibits normal wall motion before the application of the load. In this case, if the patient has normal cardiac muscle, the pump function of the heart is enhanced. Therefore, when the motion information exhibits strain on a short-axis image, the degree of increase in wall thickness is displayed in red. If, however, myocardial ischemia is induced, and a low-wall-motion region appears, since an increase in wall thickness in the corresponding area decreases, the region is displayed in blue. This makes it possible to easily discriminate normal myocardium from abnormal myocardium.

In some case, an examination for contractility recovery is performed by drug administration for a patient with a low-wall-motion region before the application of a load. In such a case, an area where contractive force is recovered is displayed in red. This allows the operator to know that the viability of this portion of the myocardium is left. In contrast, if the contractive force is not recovered, the corresponding portion is displayed in orange to yellow in accordance with the degree of the motion information of the corresponding portion (or is displayed in red to dark red and black when the magnitude of the change amount is converted into brightness). This allows the operator to easily know that the myocardium of this portion is completely necrosis.

As described above, in the first embodiment, a displacement or strain as a stable index is obtained as the motion information of a moving organ in each of phases in different load states, e.g., jogging and drug administration. A comparison parameter is computed as the difference, ratio, or standardized ratio between displacements or strain in the respective phases. Color display is then performed on the basis of the computed comparison parameter. This makes it possible to display a change before and after the application of a load with high reproducibility. This is because the signal representing the displacement or strain is more stable than the signal representing the velocity. In addition, since a displacement or strain is given on the basis of the time integration of velocity, the stability is further improved by using a peak value in a predetermined interval for the computation of a comparison parameter.

Second Embodiment

In the first embodiment described above, a comparison parameter is calculated by comparing two motion information images respectively obtained in different phases for each pixel. Owing to various state changes such as changes in slice (scan position in each phase) before and after the application of load, respiration, and heart rate, there is, however, no guarantee that the positional relationship between two motion information images as comparison targets will remain the same. A shift in the positional relationship between two motion information images may degrade the stability of a comparison parameter.

The second embodiment directed to avoid the above inconvenience will be described below.

Figure 4:
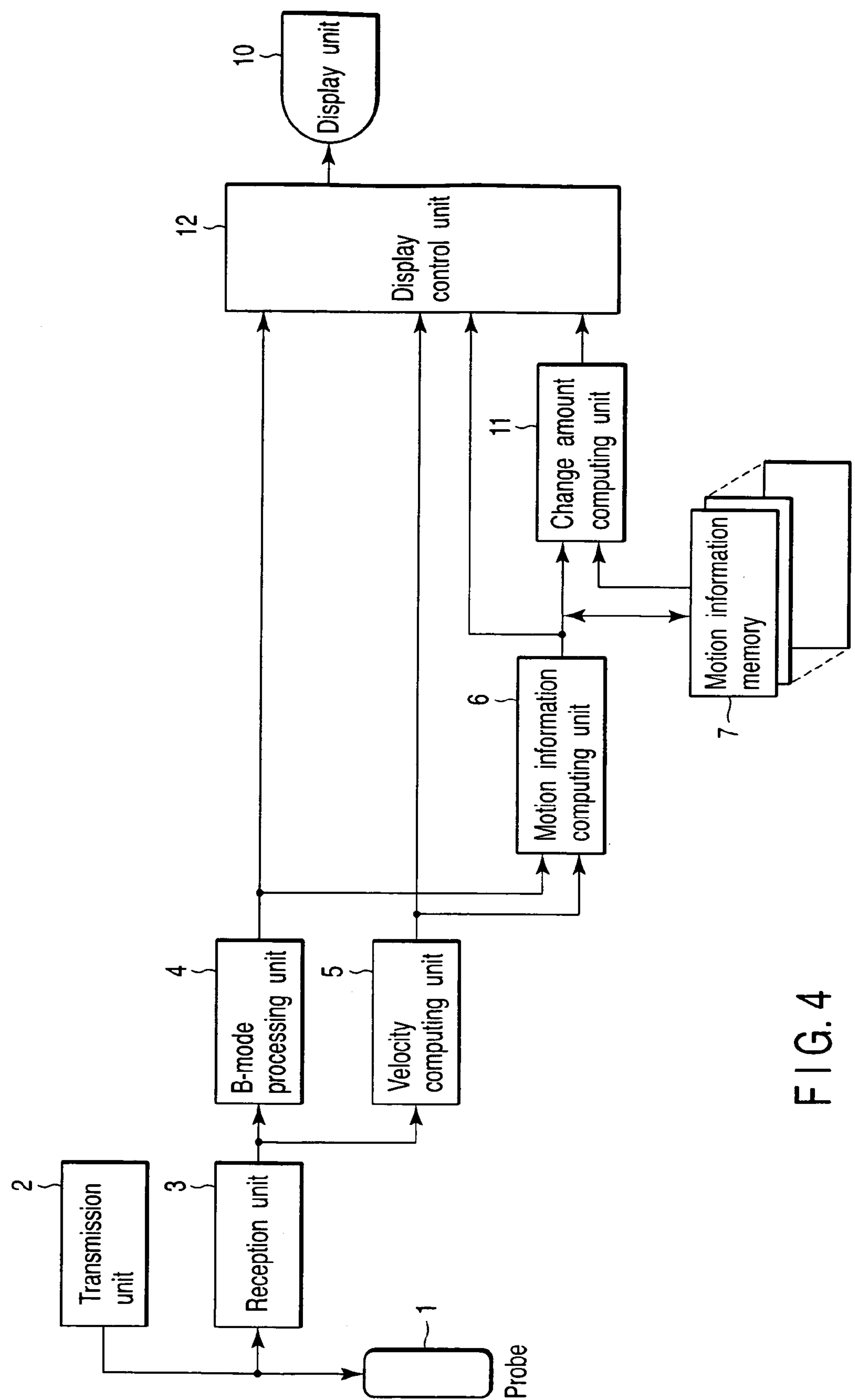
FIG. 4 is a block diagram showing the arrangement of an ultrasound diagnostic apparatus according to the second embodiment of the present invention.

FIG. 4 is a block diagram showing the arrangement of an ultrasound diagnostic apparatus according to the second embodiment. Note that the same reference numerals as in FIG. 1 denote the same parts in FIG. 4, and a detailed description thereof will be omitted.

As shown in FIG. 4, the ultrasound diagnostic apparatus of the second embodiment includes an ultrasound probe 1, transmission unit 2, reception unit 3, B-mode processing unit 4, velocity computing unit 5, motion information computing unit 6, motion information memory 7, display unit 10, change amount computing unit 11, and display control unit 12. That is, the ultrasound diagnostic apparatus of the second embodiment comprises the change amount computing unit 11 and display control unit 12 in place of the change amount computing unit 8 and display control unit 9 in the first embodiment.

FIG. 5 is a block diagram showing the concrete arrangement of the change amount computing unit 11.

As shown in FIG. 5, the change amount computing unit 11 includes a segment setting unit 11*a*, comparison computing unit 11*b*, and output information computing unit 11*c*.

The segment setting unit 11*a* sets segments in accordance with, for example, a user instruction. The segment setting unit 11*a* preferably displays motion information in each phase to allow the user to execute segment setting in each phase in correspondence with a position on an image. This image output is directly supplied from the segment setting unit 11*a* to the display control unit 12 and displayed by the display unit 10 to make the user check the information.

The comparison computing unit 11*b* generates a comparison parameter by comparing motion information images by using pieces of motion information in different phases which are stored in the motion information memory 7. The output information computing unit 8*b* computes the intra-segment representative value of the comparison parameter values generated by the comparison computing unit 8*a*. The output information computing unit 8*b* generates a comparison parameter image representing the computed representative value.

The display control unit 12 generates a display image which makes the user know the set state of segments on the basis of the motion information image output from the segment setting unit 11*a*. The display control unit 12 also generates a display image indicating a comparison parameter for each segment.

The operation of the ultrasound diagnostic apparatus according to the second embodiment having the above arrangement will be described next.

The operation of the ultrasound diagnostic apparatus according to the second embodiment differs from that of the ultrasound diagnostic apparatus according to the first embodiment in "5. Display of Comparison Parameter". Therefore, only operation associated with this will be described below.

A characteristic feature of the ultrasound diagnostic apparatus of the second embodiment is that the representative values of comparison parameter values in anatomically significant local segments are obtained and compared with each other in different load states. This technique is suitable for a case wherein the stability of an output is regarded more important than spatial resolution.

The output information computing unit 11*c* obtains the representative value of comparison parameter values in a segment.

Figure 6B:
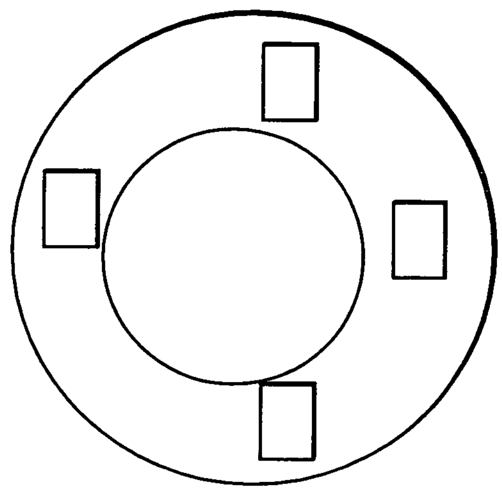
FIGS. 6A and 6B are views each showing an example of local segment setting.
Figure 6A:
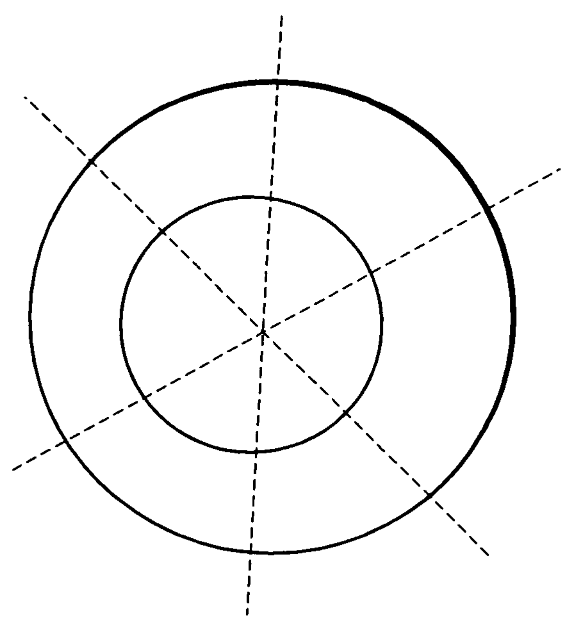

As an example of such anatomically significant segmentation, ASE (American Society of Echocardiography) segmentation schematically shown in FIG. 6A is available. In addition, a similar effect can be expected from a method of providing a plurality of ROIs as shown in FIG. 6B, which simulates ASE segmentation. In practice, as the representative value of comparison parameter values, the mean value, median value, or intermediate value of comparison parameter values in a segment can be suitably used.

The output information computing unit 11*c* generates a comparison parameter image indicating the obtained representative comparison parameter value.

Figure 7C:
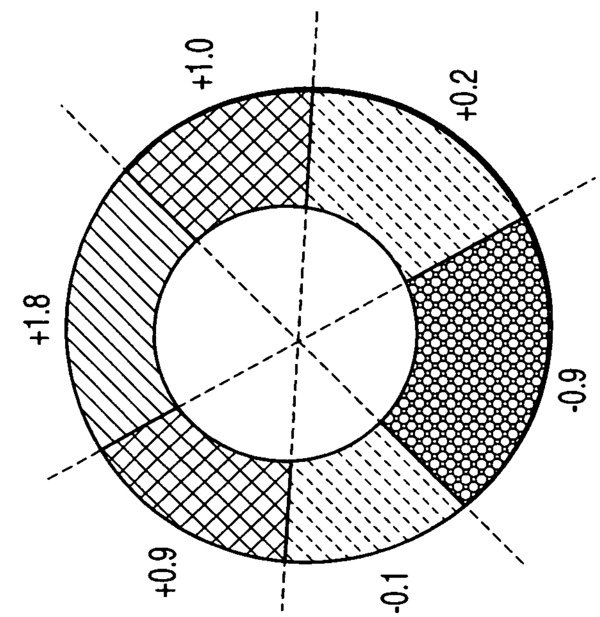
FIGS. 7A, 7B, and 7C are views each showing an example of display of representative values compared while the load state is changed for each segment in FIG. 6A.
Figure 7B:
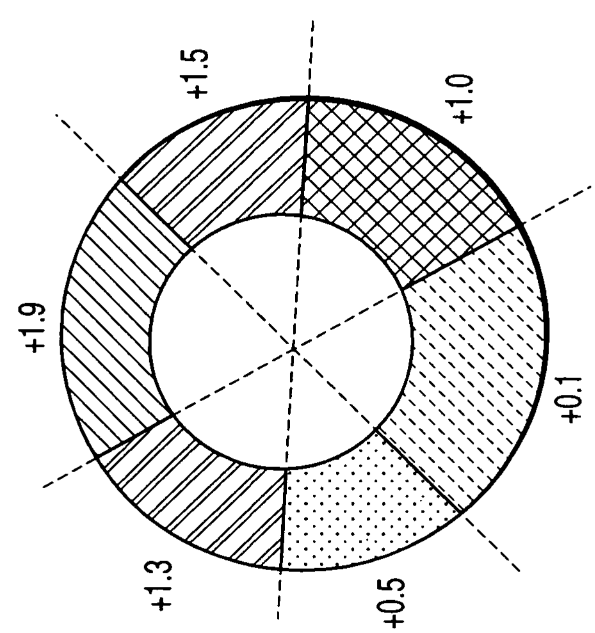
Figure 7A:
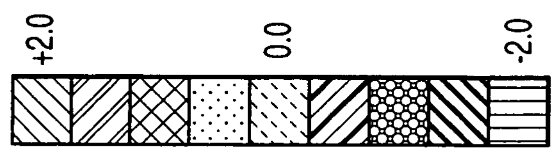

FIGS. 7A, 7B, and 7C are views each showing an example of display of representative values which are compared with each other while different load states are set for the respective segments in FIG. 6A. The above representative value is, for example, the intra-area mean value of the change amount between phases, given by expression (2), in motion information of strain. In this example, comparison parameters obtained in different load states in the respective segments are displayed by numerical values. In addition, these numerical values are color-converted with a color map like that shown in FIG. 7A, and the resultant data are displayed upon being allocated to the respective segments, thereby supporting intuitive understanding.

FIG. 7B schematically shows a comparison result between phase_1 and phase_0 at the time of application of a dobutamine load. FIG. 7C schematically shows a comparison result between phase_4 and phase_0 at the time of application of a dobutamine load. Note that phase_i and phase_j to be compared are arbitrarily combined.

With this operation, the influence of a shift in the positional relationship between two motion information images is reduced, and data in the same local area can be stably and simply compared with each other.

In addition, since each segment is an anatomically significant region or the like, the corresponding output information can be directly used as a report for diagnosis.

Third Embodiment

The third embodiment directed to avoid a deterioration in the stability of comparison parameters due to a shift in the positional relationship between two motion information images will be described.

FIG. 8 is a block diagram showing the arrangement of an ultrasound diagnostic apparatus according to the third embodiment. Note that the same reference numerals as in FIG. 1 denote the same parts in FIG. 8, and a detailed description thereof will be omitted.

As shown in FIG. 8, the ultrasound diagnostic apparatus of the third embodiment includes an ultrasound probe 1, transmission unit 2, reception unit 3, B-mode processing unit 4, velocity computing unit 5, motion information computing unit 6, motion information memory 7, display unit 10, change amount computing unit 13, and display control unit 14. That is, the ultrasound diagnostic apparatus of the third embodiment comprises the change amount computing unit 13 and display control unit 14 in place of the change amount computing unit 8 and display control unit 9 in the first embodiment.

Figure 9:
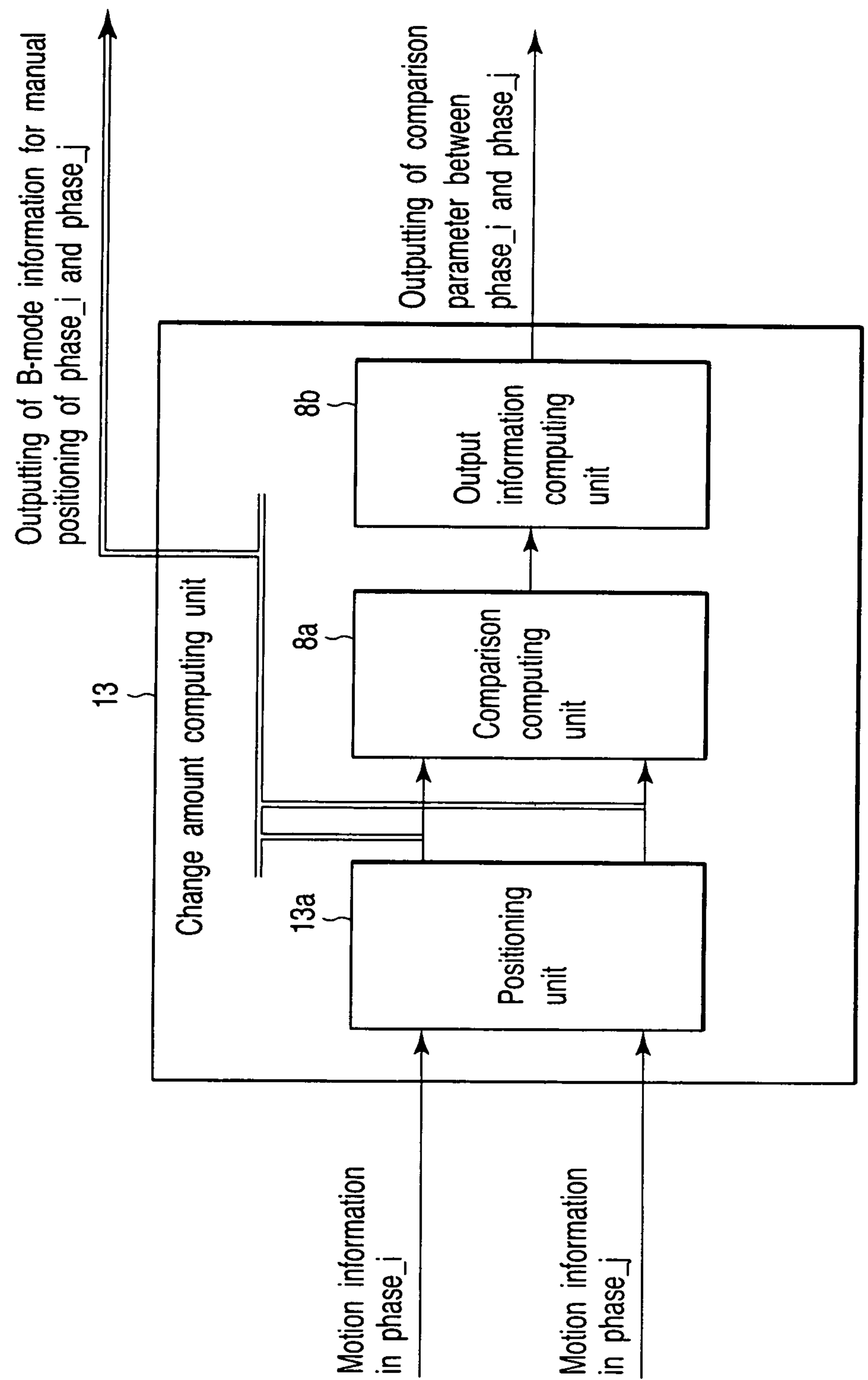
FIG. 9 is a block diagram showing the concrete arrangement of a change amount computing unit in FIG. 8.

FIG. 9 is a block diagram showing the concrete arrangement of the change amount computing unit 13. Note that the same reference numerals as in FIG. 2 denote the same parts in FIG. 9, and a detailed description thereof will be omitted.

As shown in FIG. 9, the change amount computing unit 13 includes a comparison computing unit 8*a*, output information computing unit 8*b*, and positioning unit 13*a*. That is, the change amount computing unit 13 has an arrangement equivalent to that of the change amount computing unit 8 to which the positioning unit 13*a* is added.

The positioning unit 13*a* positions two motion information images used for the calculation of a comparison parameter in accordance with a user instruction. The positioning unit 13*a* also outputs B-mode information contained in input motion information, as B-mode information for manual positioning to the display control unit 14.

The display control unit 14 has a function of generating a display image which supports the user to issue an instruction for positioning, in addition to the function of the display control unit 9 in the first embodiment. The display control unit 14 generates a display image for the above positioning operation on the basis of the B-mode information for manual positioning which is output from the positioning unit 13*a*.

The operation of the ultrasound diagnostic apparatus according to the third embodiment having the above arrangement will be described next.

A characteristic feature of the ultrasound diagnostic apparatus of the third embodiment is that the user manually adjusts the positional relationship between two motion information images as comparison targets.

The positioning unit 13*a* extracts B-mode images in the background from two motion information images as comparison targets. The position of one B-mode image is fixed, and the other B-mode image to be compared is made manually movable. The positioning unit 13*a* then moves the movable B-mode image relative to the fixed B-mode image in accordance with a user instruction. In this case, one B-mode image and the other B-mode image are colored in different colors such that when they overlap, the overlapping portion becomes white. For example, in coloring these images, green is allocated to one B-mode image, and magenta is allocated to the other B-mode image. In comparing operation, this color allocation supports the user to properly position the B-mode images by manually moving them so as to maximize a white area.

Comparison parameters are calculated and displayed in the same manner as in the first embodiment on the basis of the two motion information images after the execution of positioning in this manner.

With this operation, the influence of a shift in the positional relationship between two motion information images is reduced, and data in the same local area can be stably compared with each other.

Fourth Embodiment

The fourth embodiment directed to avoid a deterioration in the stability of a comparison parameter due to a shift in the positional relationship between two motion information images will be described.

FIG. 10 is a block diagram showing the arrangement of an ultrasound diagnostic apparatus according to the fourth embodiment. Note that the same reference numerals as in FIG. 1 denote the same parts in FIG. 10, and a detailed description thereof will be omitted.

As shown in FIG. 10, the ultrasound diagnostic apparatus of the fourth embodiment includes an ultrasound probe 1, transmission unit 2, reception unit 3, B-mode processing unit 4, velocity computing unit 5, motion information computing unit 6, motion information memory 7, display control unit 9, display unit 10, and change amount computing unit 15. That is, the ultrasound diagnostic apparatus of the fourth embodiment comprises the change amount computing unit 15 in place of the change amount computing unit 8 in the first embodiment.

FIG. 11 is a block diagram showing the concrete arrangement of the change amount computing unit 15. Note that the same reference numerals as in FIG. 2 denote the same parts in FIG. 11, and a detailed description thereof will be omitted.

As shown in FIG. 11, the change amount computing unit 15 includes a comparison computing unit 8*a*, output information computing unit 8*b*, and positioning unit 15*a*. That is, the change amount computing unit 15 has an arrangement equivalent to that of the change amount computing unit 8 to which the positioning unit 15*a* is added.

The positioning unit 15*a* automatically positions two motion information images to be used for the calculation of a comparison parameter.

The operation of the ultrasound diagnostic apparatus according to the fourth embodiment having the above arrangement will be described next.

A characteristic feature of the ultrasound diagnostic apparatus of the fourth embodiment is that the positional relationship between two motion information images as comparison targets are automatically adjusted.

The positioning unit 15*a* extracts B-mode images in the background from two motion information images as comparison targets, and performs pattern matching processing. For pattern matching, for example, a known technique like that disclosed in Jpn. Pat. Appln. KOKAI Publication No. 8-164139 can be used. In this case, the two B-mode images can be automatically and properly positioned by moving the other B-mode image to be compared to a position where the two B-mode images match most (look most similar to each other). Note that pattern matching may be performed with respect to the entire area of each B-mode image or only a partial area of each B-mode image. Pattern matching target areas may be determined in advance or determined in accordance with the designation by the user. The positioning unit 15*a* may automatically set target areas. As a technique of automatically setting target areas, for example, a technique of extracting an area of each B-mode image in which a characteristic structure appears.

A comparison parameter is then calculated and displayed in the same manner as in the first embodiment on the basis of the two motion information images positioned in this manner.

With this operation, the influence of a shift in the positional relationship between two motion information images is reduced, and data in the same local area can be stably compared with each other.

Fifth Embodiment

Each embodiment described above is directed to the value of a displacement or strain of tissue. It is, however, known that the peak time of a displacement or strain of tissue locally delays due to abnormality in the tissue such as myocardial infarction. This phenomenon is called time delay.

The fifth embodiment directed to this time delay will be described below.

Figure 12:
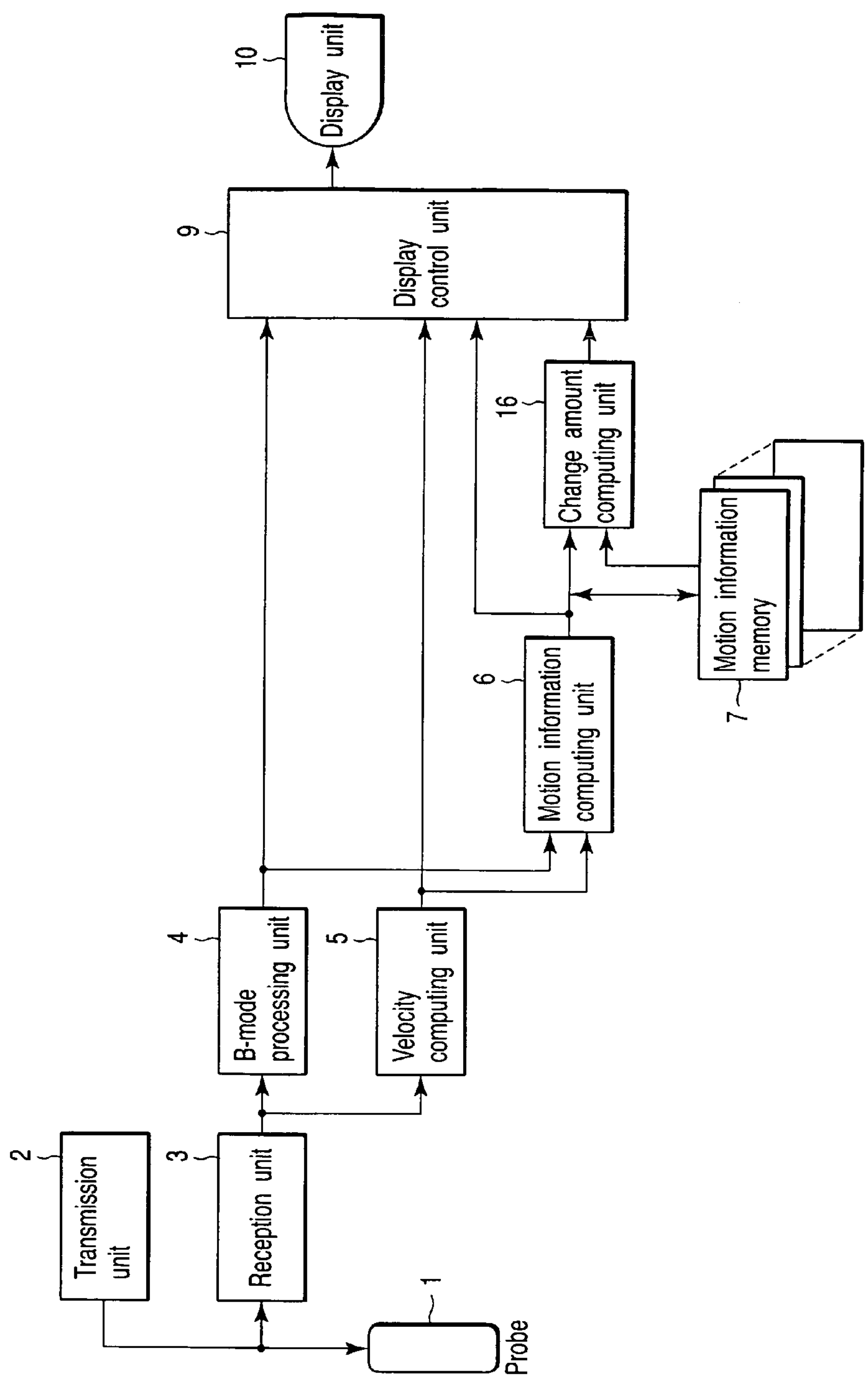
FIG. 12 is a block diagram showing the arrangement of an ultrasound diagnostic apparatus according to the fifth embodiment of the present invention.

FIG. 12 is a block diagram showing the arrangement of an ultrasound diagnostic apparatus according to the fifth embodiment. Note that the same reference numerals as in FIG. 1 denote the same parts in FIG. 12, and a detailed description thereof will be omitted.

As shown in FIG. 12, the ultrasound diagnostic apparatus of the fifth embodiment includes an ultrasound probe 1, transmission unit 2, reception unit 3, B-mode processing unit 4, velocity computing unit 5, motion information computing unit 6, motion information memory 7, display control unit 9, display unit 10, and change amount computing unit 16. The ultrasound diagnostic apparatus of the fifth embodiment comprises the change amount computing unit 16 in place of the change amount computing unit 8 in the first embodiment.

FIG. 13 is a block diagram showing the concrete arrangement of the change amount computing unit 16. Note that the same reference numerals as in FIG. 2 denote the same parts in FIG. 13, and a detailed description thereof will be omitted.

As shown in FIG. 13, the change amount computing unit 16 includes a comparison computing unit 8*a*, output information computing unit 8*b*, and peak time detection unit 16*a*. The change amount computing unit 16 has an arrangement equivalent to that of the change amount computing unit 8 to which the peak time detection unit 16*a* is added.

The peak time detection unit 16*a* detects a peak time in a cardiac time interval, for each pixel, in which a displacement or strain peak appears, with respect to each of motion information images in different phases which are stored in the motion information memory 7. The peak time detection unit 16*a* measures the required time from a predetermined reference time to a peak time in a cardiac time interval, and generates a motion information image representing the required time for each pixel.

The operation of the ultrasound diagnostic apparatus according to the fifth embodiment having the above arrangement will be described next.

The operation of the ultrasound diagnostic apparatus according to the fifth embodiment differs from that of the ultrasound diagnostic apparatus according to the first embodiment in "4. Acquisition of Comparison Parameter". Therefore, only operation associated with this will be described below.

Figure 14:
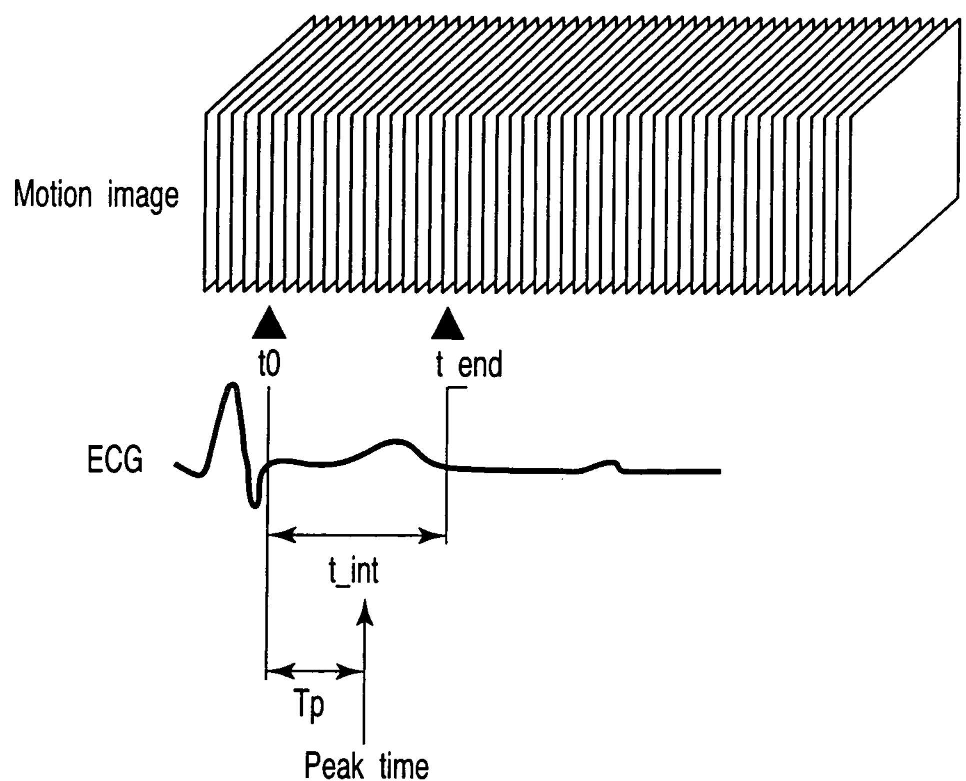
FIG. 14 is a view for explaining a required time Tp from an interval start time t0 to a peak time in a cardiac time interval t_int.

The peak time detection unit 16*a* measures, for each pixel (x, y) of a motion information image, a required time Tp from an interval start time t0 to a peak time in which a peak value (maximum or minimum value) in a cardiac time interval t_int like that shown in FIG. 14 is obtained. Note that the required time Tp may be the required time to a time in which a value of z % (z is an arbitrary number) of the maximum or minimum value is obtained.

The comparison computing unit 8*a* computes a change amount (comparison parameter) according to one of expressions (4), (5), and (6) given below from a peak time Tp(i, x, y) in phase_i and a peak time Tp(j, x, y) in phase_j.

$$Tp(j,x,y)/Tp(i,x,y) \tag{4}$$

$$Tp(j,x,y)-Tp(i,x,y) \tag{5}$$

$$\{Tp(j,x,y)-Tp(i,x,y)\}/Tp(i,x,y) \tag{6}$$

Expressions (4), (5), and (6) given above differ from expressions (1), (2), and (3) in the first embodiment only in information to be used for computations. Since the computations themselves are substantially the same as those by expressions (1), (2), and (3), the operation of the output information computing unit 8*b* is the same as that in the first embodiment.

Figure 15:
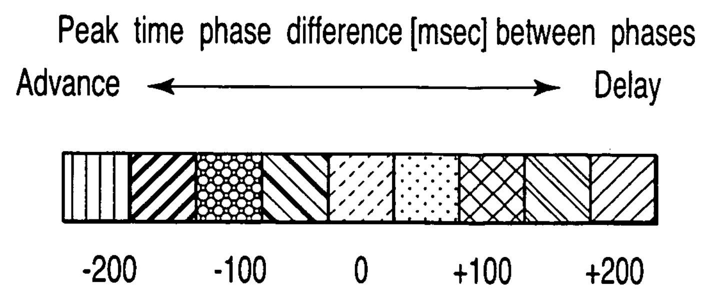
FIG. 15 is a view showing an example of a color map for color display in the fifth embodiment.

Assume that the sign "+" of the change amount given by expression (5) is expressed by a warm color (e.g., red), the sign "−" is expressed by a cold color (e.g., blue), and the magnitude of the change amount is expressed by hue (or luminance). In this case, the meaning of a color map is created as shown in FIG. 15. Assume that such a color map is used. In this case, a normal myocardium region exhibiting no change in peak time before and after the application of a load is displayed in green without no time difference. In contrast to this, a myocardium region in which a peak time associated with a local distortion is delayed (myocardium ischemia is induced) as a load is applied is gradually displayed in reddish colors. This makes it possible to sharply and easily discriminate an abnormal myocardium region from a normal myocardium region.

In an ischemic heart disease case in which even if a wall motion looks normal before the application of a load, ischemia is induced by the application of the load, and local delay of the wall motion occurs, the manner of how the local delay slightly changes before and after the application of the load can be easily grasped.

Note that the fifth embodiment can also be executed by combining characteristic arrangements in the second to fourth embodiments.

This embodiment can be variously modified as follows.

The case wherein a reception signal is obtained in a 2D space has been described. Similar procedures can be applied to a case wherein a reception signal is obtained in a 3D space, by dimensional extension.

The functions of the motion information computing unit 6, change amount computing units 8, 11, 13, 15, and 16, and display control units 9, 12, and 14 may be executed by the ultrasound image processing apparatus, implemented by a personal computer, a workstation, or the like, independently of the ultrasound diagnostic apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound image processing method of performing image processing for diagnosis of a subject to be examined on the basis of a motion velocity measured repeatedly with respect to local tissue in the subject at intervals shorter than a motion cycle of the tissue by using ultrasound waves transmitted and received by an ultrasound probe, comprising:

acquiring information, using a motion information computing unit in an ultrasound diagnostic system, representing motion corresponding to a strain or displacement of the tissue on the basis of local time integration processing using a plurality of the measured motion velocities; and calculating a parameter value, using a change amount computing unit in the ultrasound diagnostic system, representing a change amount of motion of the tissue with a change in load on the basis of a first item of motion information representing a first peak value of a pixel in a first motion image acquired over a time interval of the motion cycle at a first phase and a second item of motion information representing a second peak value of the pixel in a second motion image acquired over the time interval of the motion cycle at a second phase, the first item of motion information being acquired before an exercise load or drug load is applied and the second item of motion information being acquired during application of the exercise load or drug load.

2. A method according to claim 1, further comprising:

acquiring a plurality of the motion-information items about different multiple time phases within the motion of the tissue, extracting motion information of a peak in the ultrasound diagnostic system, from a plurality of acquired motion information in an observation period which starts from a reference time in the motion cycle and is shorter than the motion cycle, and calculating the parameter value on the basis of the first and second items of motion information.

3. A method according to claim 1, further comprising:

acquiring items of information representing motion about different multiple time phases within the time interval, measuring a first required time from a reference time in the motion cycle until a value of the first item of motion information reaches a predetermined value and a second required time from the reference time in the motion cycle until a value of the second item of motion information reaches the predetermined value, and calculating the parameter value on the basis of the first required time and the second required time.

4. A method according to claim 1, further comprising calculating a difference, a ratio, or a standardized ratio between the two items of motion information as the parameter value.

5. A method according to claim 1, further comprising generating in the ultrasound diagnostic system, an image in which the parameter value is reflected.

6. A method according to claim 5, further comprising displaying the image using a display.

7. A method according to claim 5, further comprising generating as the image a color image expressing the change amount by a color.

8. A method according to claim 1, which further comprises adjusting a relative positional relationship between two pieces of image information each having motion information as pixel information which is acquired with respect to each of a plurality of local tissues present in a two dimensional plane or a three dimensional space scanned with the ultrasound probe, and calculating the parameter value as a value representing a change amount between pieces of pixel information at the same position in the two pieces of image information on the basis of the two pieces of image information whose positional relationship has been adjusted.

9. A method according to claim 8, wherein the positional relationship is adjusted by detecting a relative positional relationship between the two pieces of image information by performing pattern matching for entire two images represented by the two pieces of image information or partial areas thereof, and adjusting the positional relationship to a specified relationship.

10. A method according to claim 1, further comprising calculating a second parameter value representing a change amount between pieces of pixel information at the same position in two pieces of image information, on the basis of image information having, as pixel information, motion information acquired with respect to each of a plurality of local tissues present in a two dimensional plane or a three dimensional space scanned with the ultrasound probe, and selecting a representative value in an local segment or a local region of interest set in the two dimensional plane or the three dimensional space from the calculated parameter values.

11. A method according to claim 1, comprising a computer configured to include the motion information computing unit and change amount computing unit.

12. An ultrasound diagnostic apparatus, comprising:

a computer configured to execute instructions to generate an image of a subject exposed to ultrasound waves from an ultrasound probe; and a memory storing the instructions which when executed by the computer results in generating the image by performing the following operations:

repeatedly measuring a motion velocity of local tissue of the subject by using ultrasound waves transmitted and received by the ultrasound probe at intervals shorter than a motion cycle of the tissue;

acquiring information representing motion corresponding to a strain or displacement of the tissue on the basis of local time integration processing using a plurality of the motion velocities;

calculating a parameter value representing a change amount of motion of the tissue with a change in load on the basis of a first item of motion information representing a first peak value of a pixel in a first motion image acquired over a time interval of the motion cycle at a first phase and a second item of motion information representing a second peak value of the pixel in a second motion image acquired over the time interval of the motion cycle at a second phase, the first item of motion information being acquired before an exercise load or drug load is applied and the second item of motion information being acquired during application of the exercise load or drug load; and generating an image in which the parameter value is reflected.

13. An apparatus according to claim 12, comprising the computer executing instructions to perform the operations of:

acquiring a plurality of items of information representing motion about different multiple time phases within the time interval, extracting an item of a peak from a plurality of items of information acquired by the acquiring information in an observation period which starts from a reference time in the motion cycle and is shorter than the motion cycle; and calculating the parameter value on the basis of the first and second items of motion information.

14. An apparatus according to claim 12, comprising the computer executing instructions to perform the operation of:

calculating a difference, a ratio, or a standardized ratio between the two items as the parameter value.

15. An apparatus according to claim 12, further comprising a display unit which displays the image generated in which the parameter value is reflected.

16. An apparatus according to claim 15, further comprising a display control unit which generates a color image expressing the change amount by a color.

17. An apparatus according to claim 12, comprising the computer executing instructions to perform the operations of:

adjusting a relative positional relationship between two pieces of image information each having motion information as pixel information which are acquired by with respect to each of a plurality of local tissues present in a two dimensional plane or a three dimensional space scanned with the ultrasound probe, and calculating a second parameter value representing a change amount between pieces of pixel information at the same position in the two pieces of image information on the basis of the two pieces of image information whose positional relationship is adjusted by the adjusting of the relative positional relationship.

18. An apparatus according to claim 17, comprising the computer executing instructions to perform the operations of:

detecting a relative positional relationship between the two pieces of image information by performing pattern matching for entire two images represented by the two pieces of image information or partial areas thereof, and adjusting the positional relationship to a specified relationship.

19. An apparatus according to claim 12, comprising the computer executing instructions to perform the operation of:

selecting a representative value in an anatomically significant local segment or a local region of interest set in a two dimensional plane or a three dimensional space.

20. An ultrasound diagnostic apparatus, comprising:

a computer configured to execute instructions to generate an image of a subject exposed to ultrasound waves from an ultrasound probe; and a memory storing the instructions which when executed by the computer results in generating the image by performing the following operations:

repeatedly measuring a motion velocity of local tissue of the subject by using ultrasound waves transmitted and received by the ultrasound probe at intervals shorter than a motion cycle of the tissue;

acquiring information representing motion corresponding to a strain or displacement of the tissue on the basis of local time integration processing using a plurality of the motion velocities measured by the velocity computing unit; and calculating a parameter value representing a change amount of motion of the tissue with a change in load on the basis of a first item of motion information and a second item of motion information, the first item of motion information being acquired before an exercise load or drug load is applied and the second item of motion information being acquired during application of the exercise load or drug load, and a time detection unit, wherein the computer is further configured to execute instructions to perform acquiring a plurality of the items of information representing motion about different multiple time phases within one of the intervals, the time detection unit measures a first time period from a reference time in the motion cycle until a time when a value of the first item of motion information reaches a predetermined value during the motion cycle and a second time period from the reference time in the motion cycle until a time when a value of the second item of motion information reaches the predetermined value during the motion cycle, and the computer is further configured to execute instructions to perform calculating the parameter value on the basis of the first time period and the second time period.

* * * * *